United States Patent
Li

(10) Patent No.: US 10,234,372 B2
(45) Date of Patent: Mar. 19, 2019

(54) NMR ANALYSIS SYSTEM AND METHOD FOR POROUS MEDIA

(71) Applicant: IROCK TECHNOLOGIES CO., LTD., Beijing (CN)

(72) Inventor: Danyong Li, Beijing (CN)

(73) Assignee: IROCK TECHNOLOGIES CO., LTD., Beijing (CN)

( * ) Notice: Subject to any disclaimer, the term of this patent is extended or adjusted under 35 U.S.C. 154(b) by 61 days.

(21) Appl. No.: 15/407,256

(22) Filed: Jan. 17, 2017

(65) Prior Publication Data
US 2017/0122858 A1    May 4, 2017

Related U.S. Application Data

(63) Continuation of application No. PCT/CN2015/087251, filed on Aug. 17, 2015.

(51) Int. Cl.
| | |
|---|---|
| G01N 1/40 | (2006.01) |
| G01N 15/08 | (2006.01) |
| G01N 24/08 | (2006.01) |
| G01R 33/44 | (2006.01) |
| G01N 33/24 | (2006.01) |

(52) U.S. Cl.
CPC .......... *G01N 15/088* (2013.01); *G01N 24/08* (2013.01); *G01N 24/081* (2013.01); *G01N 33/241* (2013.01); *G01R 33/448* (2013.01); *G01N 2015/0846* (2013.01)

(58) Field of Classification Search
CPC .................................................. G01N 15/088
USPC ............................................................ 702/2
See application file for complete search history.

(56) References Cited

U.S. PATENT DOCUMENTS

| | | | |
|---|---|---|---|
| 8,965,740 B2 | 2/2015 | Safonov | |
| 2003/0160612 A1* | 8/2003 | Yablonskiy | G01R 33/56341 324/309 |
| 2011/0066404 A1* | 3/2011 | Salazar-Tio | G01V 11/00 703/1 |
| 2016/0018504 A1* | 1/2016 | Magin | A61B 5/055 324/309 |
| 2016/0139291 A1* | 5/2016 | Saidian | G01V 3/32 324/303 |

FOREIGN PATENT DOCUMENTS

CN        103513285 A        1/2014

OTHER PUBLICATIONS

Grebenkov, "NMR survey of reflected Brownian motion," Aug. 17, 2007, Review of Modern Physics, vol. 79, pp. 1077-1137.*

(Continued)

*Primary Examiner* — Ricky Ngon
(74) *Attorney, Agent, or Firm* — Syncoda LLC; Feng Ma

(57) ABSTRACT

Nuclear magnetic resonance (NMR) simulations of a porous medium are provided based on physical data such as CT images. A method of evaluating the surface relaxation of the porous medium based on random-walk NMR simulations includes a novel algorithm to derive the absorption probabilities of the random walkers, and algorithms that can evaluate more accurately the surface area and reduce the voxel discretization effect. The methods can be applied to conventional porous media as well as unconventional porous media such as reservoir rocks with high surface-to-volume ratios, for example tight sandstones or shale.

19 Claims, 7 Drawing Sheets

(56) References Cited

OTHER PUBLICATIONS

Toumelin et al., "Random-walk technique for simulating NMR measurements and 2D NMR maps of porous media with relaxing and permeable boundaries," Jun. 17, 2007, Journal of Magnetic Resonance 188, pp. 83-96.*

International Search Report and Written Opinion dated May 12, 2016 in PCT/CN2015/087251.

* cited by examiner

FIG. 5A
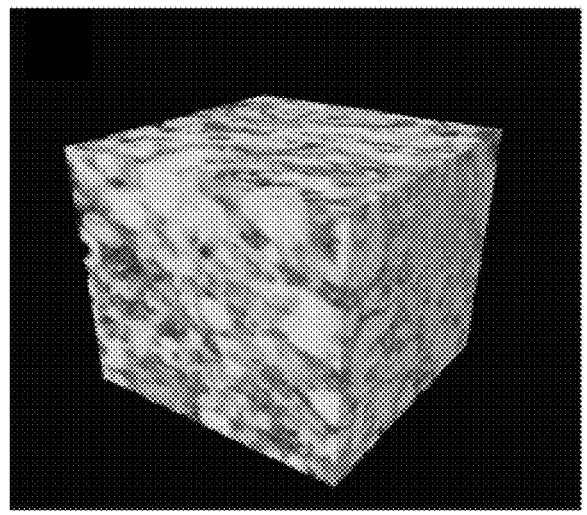
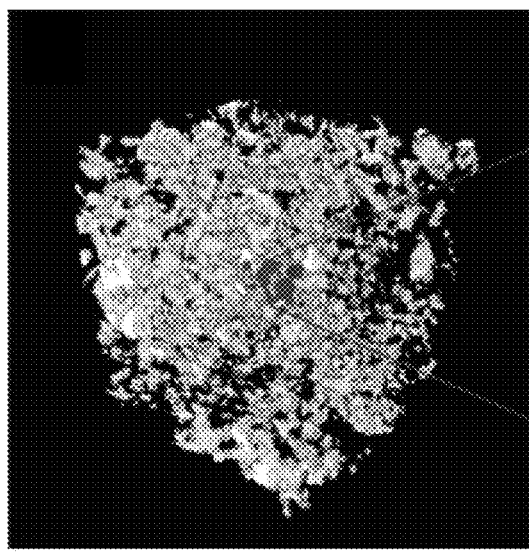
FIG. 5B
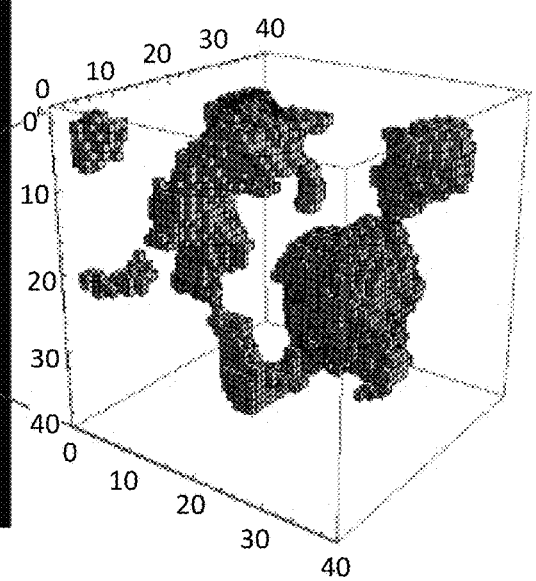
FIG. 5C

NMR ANALYSIS SYSTEM AND METHOD FOR POROUS MEDIA

CROSS-REFERENCE TO RELATED APPLICATION

The present application is a continuation of, and claims priority to, PCT/CN2015/087251 filed on Aug. 17, 2015, the disclosure of which is hereby incorporated by reference in its entirety.

BACKGROUND

Nuclear magnetic resonance (NMR) is a powerful tool in probing the structures and petrophysical properties of porous and permeable media such as rocks, soil, zeolites, and biological tissues, and has been widely used in hydrology, petroleum engineering, environment engineering, biomedical research, and clinical settings.

SUMMARY

In an aspect, systems and methods are provided to facilitate characterization of porous media. For example, a pore size distribution can be determined for a porous medium. In another example, material properties such as surface relaxation parameters can be derived. Such characterizations can then be utilized to obtain flow properties in the porous media. Based on the properties/parameters, hydrocarbon exploration can be performed with higher accuracies, for example. In the biomedical field, more accurate imaging can be obtained to thereby facilitate improved treatment plans.

Various embodiments disclosed herein employ NMR simulations based on physical data, such as computed tomography (CT) images, to derive material properties and apply the derived properties to hydrocarbon exploration, logging, biomedical diagnostics and treatment, particularly where NMR imaging is not available or is not sufficient to facilitate the derivation of the parameters.

According to some embodiments, NMR process can be simulated with Random-Walk simulations (e.g., Talabi, O., Alsayari, S., Iglauer S. and Blunt, M. J., *J. of Petro. Sci. & Eng.* 67, 168-178 (2009), Toumelin, Torres-Verdin and Chen, *SPE Res. Eva. & Eng*, 234 (2003), Toumelin, Torres-Verdin, Sun and Dunn, *Journal of Magnetic Resonance* 188, 83-96 (2007)). In such simulations, an expression of "killing probability" can be used to describe the decrease rate of random walkers.

For example, in digital rock physics, surface relaxation of NMR decay on a 3D porous media can be simulated with Random-Walker methods, where Brownian walkers representing the magnetized nuclei are absorbed by the solid surface under an interfacial absorption probability.

In a conventional method (see, e.g., Bergman, Dunn, Schwartz and Mitra, *Phy. Rev. E* 51, 3393 (1995)), the killing probability is derived based on the assumption of random walkers hitting a planar surface. However, this neglects the discretized voxel effect and thus often requires unphysical adjustment of input parameters in order to obtain reasonable simulation results.

Some unconventional reservoir rock types, such as tight sandstones or shale, may have large fractions of micro pores that have very tight and tortuous pore spaces with a high surface-to-volume ratio. As such, it may be difficult to study these unconventional rocks with NMR simulations using conventional methods.

Previous simulations with Random-Walker methods usually neglect the blocky voxel appearance of 3D pore spaces, resulting in over-estimation of the surface area, particularly for unconventional reservoir rocks that have high surface-to-volume ratios (S/V). This may require arbitrary adjustments of the interfacial absorption probability by tuning the value of the Surface Relaxivity Strength (SRS) in order to reproduce and predict "real" experimental measurements. However, this arbitrary adjustment deviates from the fact that SRS is a rock-dependent physical property.

According to some embodiments, in Random-Walk NMR simulations, the decrease of random walkers is employed to simulate the transverse decay of magnetization. In the simulations, the random walkers are controlled by an absorption probability at the solid grain surfaces, usually referred to as the killing probability. The killing probability is proportional to the surface relaxivity, the random walker step size, and is inversely proportional to the bulk diffusivity.

Various embodiments disclosed herein provide methods for NMR simulations of a porous medium, and take into account on non-planar boundaries. The methods can be suitable for all types of porous media, and are even more advantageous over conventional methods when applied to porous media having high S/V values, such as unconventional rock types that have high S/V values.

According to some implementations, a method for evaluating surface relaxation of a porous medium by means of random-walk NMR simulation is provided. The uncertainties in the previously-used killing probability approaches are greatly reduced. For example, in some embodiments, an improved killing probability is derived based on the physical process of transverse magnetization decay, and can include the S/V and the global hitting probability of the entire pore space geometry. This novel approach to the killing probability can be applied to any rock type, and has particularly significant advantages over conventional methods when applied to porous media of high S/V.

In some implementations, methods are provided to help evaluate the surface area of the porous space more accurately, thereby reducing the voxel discretization effect.

According to some embodiments, a method is provided including:

(a) seeding a plurality of random walkers representing magnetized nuclei into porous space of the porous medium to simulate diffusive Brownian motions of the plurality of random walkers, wherein decrease of the number of the random walkers is used to simulate transverse decay of magnetization as if measured by NMR; and (b) inferring an interfacial absorption probability of solid grain surface of the porous medium by deriving a killing probability based on the equation:

$$\gamma = \frac{\rho \epsilon^2 S}{6 D_0 h V} \qquad (i)$$

wherein $\gamma$ is the killing probability for the plurality of random walkers to be absorbed by the grain surface of the porous medium; $D_0$ is the bulk fluid diffusivity, and $\epsilon$ is a diffusion distance of the walkers within a time step, as described in the laws of Brownian motion of spatial diffusive particles in a 3D space; $h$ is a global probability for the random walkers to hit the grain surface of the porous medium; $\rho$ is the surface relaxivity, $S$ is pore space surface area, and $V$ is the pore space volume of the porous medium.

In some embodiments, the pore surface area S is evaluated by an optimized marching cubes algorithm By interpolating a virtual smoothed surface along discretized solid-pore interfaces of the porous medium, the plurality of random walkers hitting the grain surfaces of the porous medium can be determined by judging whether the plurality of random walkers cross the virtual smoothed surface.

In some embodiments, the global probability can be calculated as $$h = \sum_{i=1}^{N}(1-Z_i)(h_s \sum_{s=1}^{6} Z_i^s + h_c \sum_{c=1}^{8} Z_i^c + h_e \sum_{e=1}^{12} Z_i^e) \qquad (ii)$$

where $Z_i$ is voxel registration of the i-th voxel of a 3D image (such as that obtained from CT scanning) with $Z_i=0$ for a void and $Z_i=1$ for a solid grain; $Z_i^s$ ($Z_i^c$ or $Z_i^e$) are the 6 (or 8 or 12, etc.) sided (corner or edge) neighboring voxels of $Z_i$, and $h_s$, $h_c$ and $h_e$ are constant probabilities of the random walkers in voxel $Z_i$ jumping into sided, corner, and edge voxels, respectively.

The methods as disclosed above can be applied to analyze any rock types, such as soil, zeolite, or an unconventional reservoir rock having a high surface-to-volume ratio (e.g., carbonate stone, sandstone, or shale). The methods can also be applied in other areas of applications, such as to biological samples.

According to some embodiments, a method of characterizing a porous medium using NMR simulations can include the steps of:

(a) obtaining CT data for the porous medium; and (b) determining characteristics of the porous medium by NMR simulations based on the CT data, including a substep of utilizing the method for evaluating surface relaxation of the porous medium.

The method can be applied to determine the characteristics of a porous medium, such as petrophysical structure (e.g., a 3D pore network), a petrophysical property (e.g., porosity, pore size distribution, permeability, water saturation, or wettability), and a pertrophysical process (e.g. single or multi-phase fluid flow, or radionuclide transport in the porous medium by diffusion and migration) of the porous medium. These characteristics may also subject to numerical modeling.

The methods according to some embodiments can have one or more advantages over conventional methods for simulating NMR in the porous space of a sample. Based on physical data such as X-ray CT images of the porous media, and incorporating the following algorithms, uncertainties associated with the conventional methods can be significantly reduced.

For example, an improved killing probability is derived based on the physical process of transverse magnetization decay according to some embodiments. The improved killing probability effectively includes the surface-to-volume ratio and the global hitting probability of the entire pore space geometry, and can thus be applied to any rock types.

In another example, a novel algorithm is provided to more accurately evaluate the surface area and reduce the voxel discretization effect.

The NMR simulations according to embodiments disclosed herein can be verified by testing on both standard geometrical pore spaces and digital images of realistic rock samples of various rock types. It can be shown that the erroneous T2 distribution based on conventional simulations can be successfully corrected.

Other aspects and advantages of the claimed embodiments will become apparent from the following description and the attached claims.

BRIEF DESCRIPTION OF THE DRAWINGS

FIGS. 5A-5E illustrate a Random-Walk NMR simulation on a micro CT (MCT) image with pixel sizes from about 0.5 microns to about 25 micrometers according to some embodiments. Specifically, FIG. 5A illustrates a typical MCT greyscale image of a porous medium sample, with the lighter areas indicating the high-density grains and the darker-area indicating the pores. FIG. 5B illustrates the segmented pore spaces extracted from the grey-scale image. FIG. 5C illustrates a zoom-in of a part of the pore space, showing that the pore space is compiled by cubic voxels.

FIG. 5D illustrates random walkers seeded into the pore space. FIG. 5E illustrates the track of one random walker in one pore space.

DETAILED DESCRIPTION

Figure 1A:
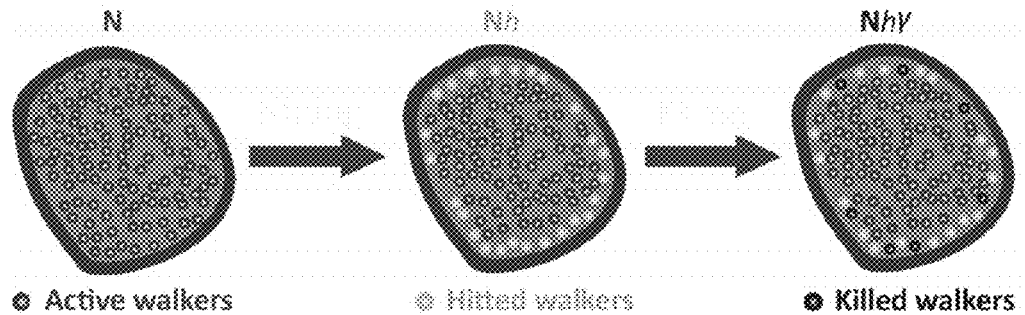
FIG. 1A illustrates the decrease of the number of random walkers in a pore space.

Nuclear magnetic resonance (NMR) occurs when an ensemble of spinning hydrogen protons undergoing Larmor precession in a uniform magnetic field $B_0$ are tilted by an oscillating magnetic field pulse $B_1(t)$ with an oscillation frequency the same as the Larmor precession frequency and perpendicular to $B_0$. The net macroscopic magnetization $M_0$ previously along the direction of $B_0$ is tilted away from its longitudinal direction to the transverse plane. As the magnetic pulse is turned off, the tilted magnetization relaxes back to its longitudinal direction and the transverse component of macroscopic magnetization M follows an exponential decay (see, e.g., Bloch, F., "Nuclear Induction", *Physical Review* 70, 460 (1946)), $$M_\perp(t) = M_\perp(0) e^{-t/T_2} \qquad (1)$$

where $T_2$ reflects the rate of the magnetization decay. The larger the value of $T_2$ is, the slower the magnetization decays. $T_2$ can be determined, for example, by three effects: bulk relaxation, surface relaxation, and bulk relaxation, and can be defined as: (see, e.g., Bloembergen, N., Purcell, E. M. and Pound, R. V., "Relaxation Effects in Nuclear Magnetic Resonance Absorption", *Physical Review* 73, 679 (1948))

$$\frac{1}{T_2} = \frac{1}{T_{2bulk}} + \frac{1}{T_{2surface}} + \frac{1}{T_{2diffusion}} \quad (2)$$

In a pore space of a rock sample, where the scale satisfies the fast diffusion limit, the surface relaxation time $T_{2surface}$ is related to the mineralogy on the pore solid surface and the surface-to-volume ratio of the pore space (see, e.g., Brownstein, K. R. and Tarr, C. E., "Importance of classical diffusion in NMR studies of water in biological cells", *Physical Review A* 19, 2446 (1979)), $$\frac{1}{T_{2surface}} = \rho \frac{S}{V} \quad (3)$$

where $\rho$ is the surface relaxivity, which can be an input parameter; S is the pore surface area, which is often unknown; and V is the pore space volume (e.g., pore-voxel counting).

In terms of field applications, $T_2$ is directly related to pore sizes. For example, the higher is $T_2$, the larger the pore sizes. Therefore, based on the magnetization decay signal curves, $T_2$ can be determined, and as a result the pore size distribution can be determined. In a realistic porous medium, the sizes of pores can vary from small (micro pores) to large (macro pores). The magnetization decay curves can contain the signals from all sizes, and $T_2$ plots can reflect the volume fraction of all pore sizes.

According to some embodiments, the surface relaxation described by Equation (1) can be simulated by Random-Walk methods, in which an ensemble of random walkers representing the spinning hydrogen protons are seeded into the porous space to simulate the diffusive Brownian motions (see, e.g., Bergman, D. J., Dunn, K. J., Schwartz, L. M. and Mitra, P. P., "Self-diffusion in a periodic porous medium: A comparison of different approaches," *Physical Review E* 51, 3393 (1995)). The random walkers moving toward the voxels adjacent to the solid-void boundaries can be absorbed by the solid interface, leading to the decrease of the number of random walkers, analogous to the surface relaxation process in which the spinning nuclei is relaxed by interaction with the solid grain surface.

Figure 1B:
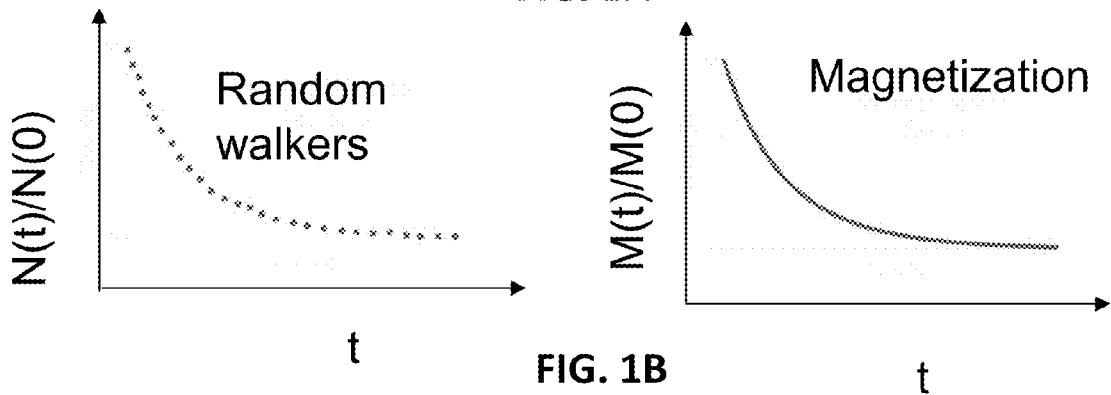
FIG. 1B compares the numerical simulation of the decrease of the random walker number with the theoretical curve of a magnetization decay.

FIG. 1A illustrates the decrease of the number of random walkers in a pore space resulting from two steps: (i) the random walkers adjacent to the solid grain surface hitting the surface, and (ii) a fraction of the walkers that hit the surface are "killed" by the surface. FIG. 1B compares the numerical simulation of the random walker number decrease with the theoretical curve of magnetization decay.

More specifically, initially a number of N random walkers are uniformly seeded into a 100% wetting phase saturated pore space. After an infinitesimal time, the number of random walkers decreases by $Nh\gamma$, where h is the global probability of random walkers hitting the pore surface, and $\gamma$ is the probability of random walkers being absorbed by the surface. Relating the decrease of random walker number with the decay of magnetization in Equation (1), it can be obtained that $$h\gamma = \frac{\Delta t}{T_2} \quad (4)$$

In the method according to some embodiments, the time step can be determined by the laws of Brownian motions of spatial diffusive particles in a 3D space. Therefore, Equation (4) can be rewritten as the expression for killing probability, $$\gamma = \frac{\rho \epsilon^2 S}{6 D_0 h V} \quad (5)$$

where $D_0$ is the bulk fluid diffusivity, which can be a physical constant; and $\epsilon$ is the diffusion distance of random walkers within a time step, e.g., a random walking step size, which can be fixed.

Effective implementation of Equation (5) into the whole process of NMR simulations may need both accurate evaluation of the surface area S and the global hitting probability of the pore space. According to some embodiments, an optimized marching cubes algorithm (see, e.g., Lindblad, J. and Nystrom I., "Surface Area Estimation of 3D Digitized Objects Using Local Computations") can be employed to evaluate the pore space surface area by interpolating a virtual smoothed surface along the discretized solid-pore interfaces. Random walkers hitting the surface can be determined by judging whether the random walkers cross this virtual surface. The hitting probability h depends on the structural geometry of the pore space and can be calculated as $$h = \Sigma_{i=1}^{N}(1-Z_i)(h_s\Sigma_{s=1}^{6}Z_i^s + h_c\Sigma_{c=1}^{8}Z_i^c + h_e\Sigma_{e=1}^{12}Z_i^e) \quad (6)$$

where $Z_i$ is the voxel registration of the i-th voxel of a 3D image with $Z_i=0$ for void and $Z_i=1$ for solid grain. $Z_i^s$ ($Z_i^c$ or $Z_i^e$) are the 6 (or 8 or 12, etc.) sided (corner or edge) neighboring voxels of $Z_i$, and $h_s$, $h_c$ and $h_e$ are the constant probabilities of random walkers in voxel $Z_i$ jumping into sided, corner, and edge voxels, respectively.

The methods for simulating NMR in a porous space of a rock sample based on the X-ray CT images according to some implementations disclosed herein can have one or more advantages over conventional methods. For example, the algorithm can evaluate more accurately the surface area, and thus reduce the voxel discretization effect. The methods can also reduce the uncertainties in the previously-used killing probability approaches in NMR simulation.

The killing probability according to some embodiments disclosed herein can be derived based on the physical process of transverse magnetization decay, which effectively includes the S/V and the global hitting probability of the entire pore space geometry. As such, the novel techniques disclosed herein can be applied to any rock types.

The NMR simulations can be verified by testing on both standard geometrical pore spaces and digital images of realistic rock samples of various rock types. It can be shown that the previously-erroneous T2 distribution is successfully corrected.

Figure 2:
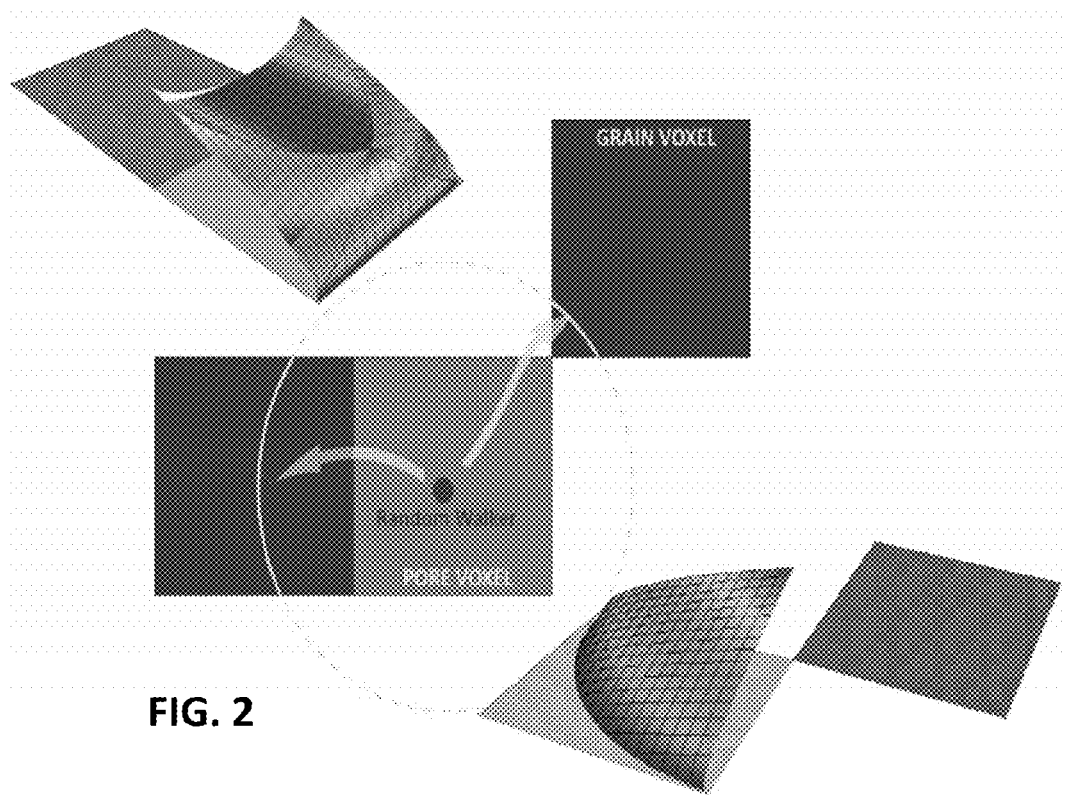
FIG. 2 shows the probability distribution (the curved contour) of one random walker in a pore voxel hitting one of the surface of the grain voxel.

The improved mathematical derivation of the hitting probability (which describes the probability of a random walker in a pore voxel jumping into a pore surface voxel) according to some embodiments disclosed herein can be illustrated by FIG. 2. FIG. 2 shows the probability distribution (the curved contour) of one random walker in a pore voxel hitting onto one of the surface grain voxel.

Figures 3, 4A:
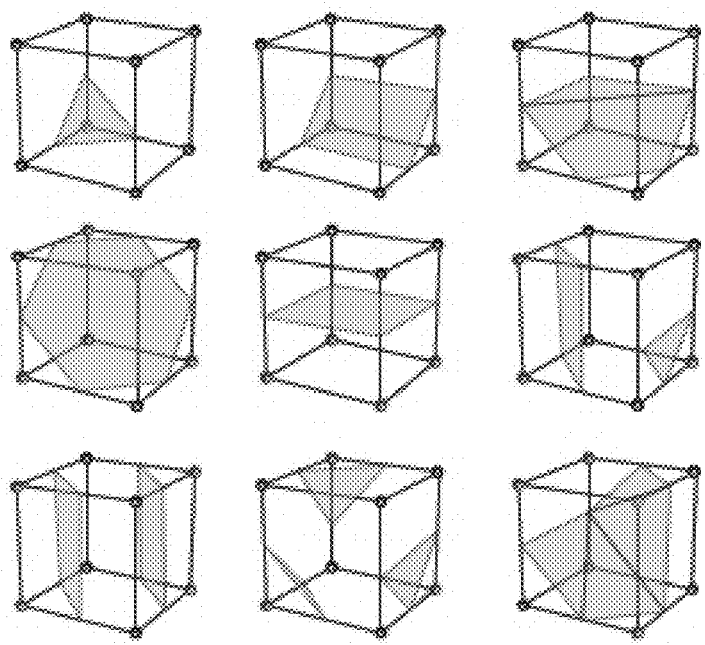
FIG. 3 shows the averaged hitting probabilities of a random walker in a pore voxel hitting onto a grain voxel for the 2D and the 3D cases.
FIG. 4A illustrates typical marching cube polygon configurations used to reduce the discretized voxel effect of pore space surfaces.

FIG. 3 shows the averaged hitting probabilities of a random walker in a pore voxel hitting onto a grain voxel for 2D and 3D cases.

According to some implementations, a more accurate evaluation of pore surface areas using an optimized marching cube algorithm (see, e.g., Lindblad, J. and Nystrom I., "Surface Area Estimation of 3D Digitized Objects Using Local Computations") can be employed to smooth the discretized digital images. FIG. 4A illustrates typical marching cube polygon configurations used to reduce the discretized voxel effect of pore space surfaces.

Figure 4B:
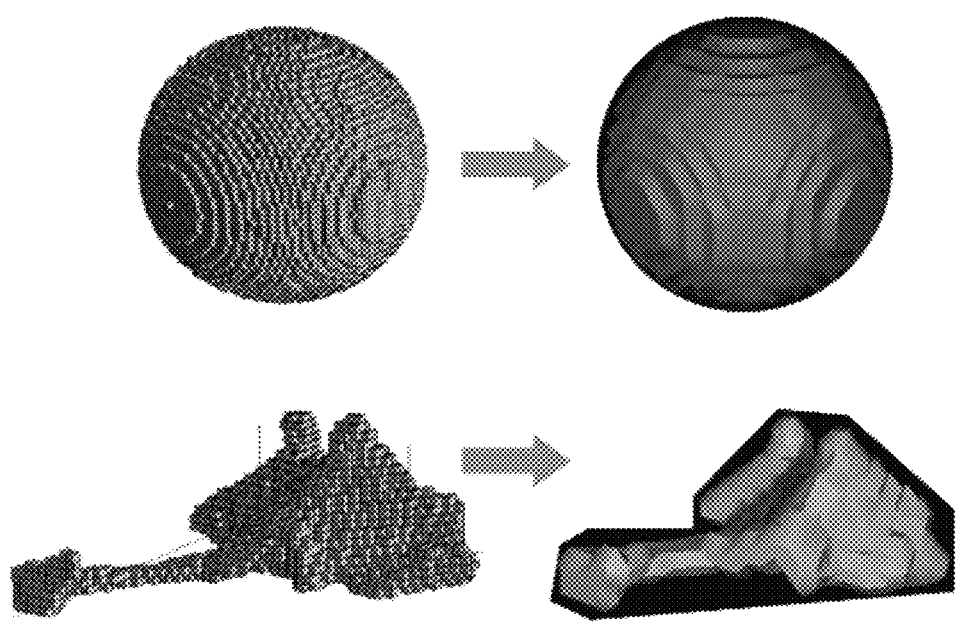
FIG. 4B shows that the algorithms according to some embodiments disclosed herein for pore surface smoothing work effectively on curved surfaces such as a sphere (upper panel) and an irregular pore space (lower panel).

FIG. 4B illustrates that the algorithms according to some embodiments disclosed herein for pore surface smoothing work effectively on curved surfaces such as a sphere (upper panel) and an irregular pore space (lower panel).

FIGS. 5A-5E illustrate a Random-Walk NMR simulation based on MCT images according to some embodiments of the disclosure.

Figures 5D, 5E:
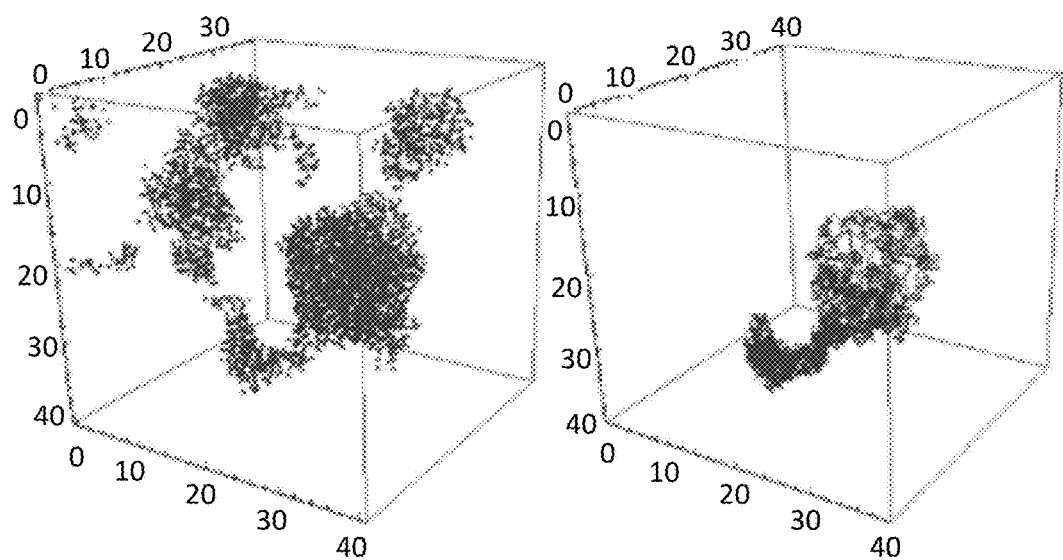

Specifically, FIG. 5A illustrates a typical MCT grey-scale image of a porous medium sample, with lighter areas indicating the high-density grains and darker areas indicating the pores. FIG. 5B illustrates the segmented pore space extracted from the greyscale image. FIG. 5C illustrates a zoom-in of a part of the pore space, which shows the pore space is compiled by cubic voxels. FIG. 5D illustrates random walkers seeded into the pore space. FIG. 5E illustrates the track of one random walker in one pore space.

Table 1 shows some simulation results on standard geometrical pore space illustrating the improved evaluation of surface area and T2 for curved surfaces. The image size as been chosen to have $200^3$ voxels, with a surface relaxivity $\rho=3.0$ μm/s.

TABLE 1

Some simulation results for cubic pores and spherical pores.

Cubic Pore

| Length (μm) | $S_{th}$ (μm$^2$) | $T2_{th}$ (ms) | $S_{old}$ (μm$^2$) | $T2_{old}$ (ms) | $S_{new}$ (μm$^2$) | $T2_{new}$ (ms) |
|---|---|---|---|---|---|---|
| 10.0 | 600.0 | 555.6 | 600.0 | 543.3 | 564.1 | 605.5 |
| 20.0 | 2400.0 | 1111.1 | 2400.0 | 1117.7 | 2329.0 | 1174.6 |
| 50.0 | 15000.0 | 2777.8 | 15000.0 | 2802.9 | 14820.0 | 2923.1 |
| 100.0 | 60000.0 | 5555.6 | 60000.0 | 5672.9 | 59650.0 | 5906.9 |

Spherical Pore

| Radius (μm) | $S_{th}$ (μm$^2$) | $T2_{th}$ (ms) | $S_{old}$ (μm$^2$) | $T2_{old}$ (ms) | $S_{new}$ (μm$^2$) | $T2_{new}$ (ms) |
|---|---|---|---|---|---|---|
| 5.0 | 314.2 | 555.6 | 486.0 | 424.0 | 341.0 | 516.5 |
| 10.0 | 1256.6 | 1111.1 | 1902.0 | 937.3 | 1372.0 | 1047.9 |
| 25.0 | 7854.0 | 2777.8 | 11770.0 | 2380.8 | 8539.0 | 2654.9 |
| 50.0 | 31415.9 | 5555.6 | 47070.0 | 4827.9 | 34140.0 | 5332.8 |

Table 2 shows some simulation results on digital rock images of sanstone, carbonate, and tight gas sand stones, with a surface relaxivity $\rho=4.0$ μm/s.

TABLE 2

Simulation results for various rocks

| Sample | Image Size (voxel) | Voxel Size (μm) | Porosity (%) | $S_{old}$ (μm$^2$) | $S_{new}$ (μm$^2$) | $T2_{old}$ (ms) | $T2_{new}$ (ms) |
|---|---|---|---|---|---|---|---|
| Sand-stone | $300^3$ | 8.68 | 14.13 | 1.73E-04 | 1.28E-04 | 4438.03 | 5722.38 |
| Carbonate | $800^3$ | 4.93 | 7.82 | 7.19E-04 | 5.16E-04 | 869.82 | 1178.16 |
| Tight gas 1 | $1000^3$ | 14.30 | 1.99 | 4.42E-03 | 3.28E-03 | 3720.65 | 5323.14 |
| Tight gas 2 | $1000^3$ | 2.77 | 7.10 | 2.33E-04 | 1.67E-04 | 2306.66 | 2928.23 |
| Tight gas 3 | $1000^3$ | 1.15 | 6.59 | 2.32E-05 | 1.66E-05 | 1608.27 | 2111.32 |

Figure 6:
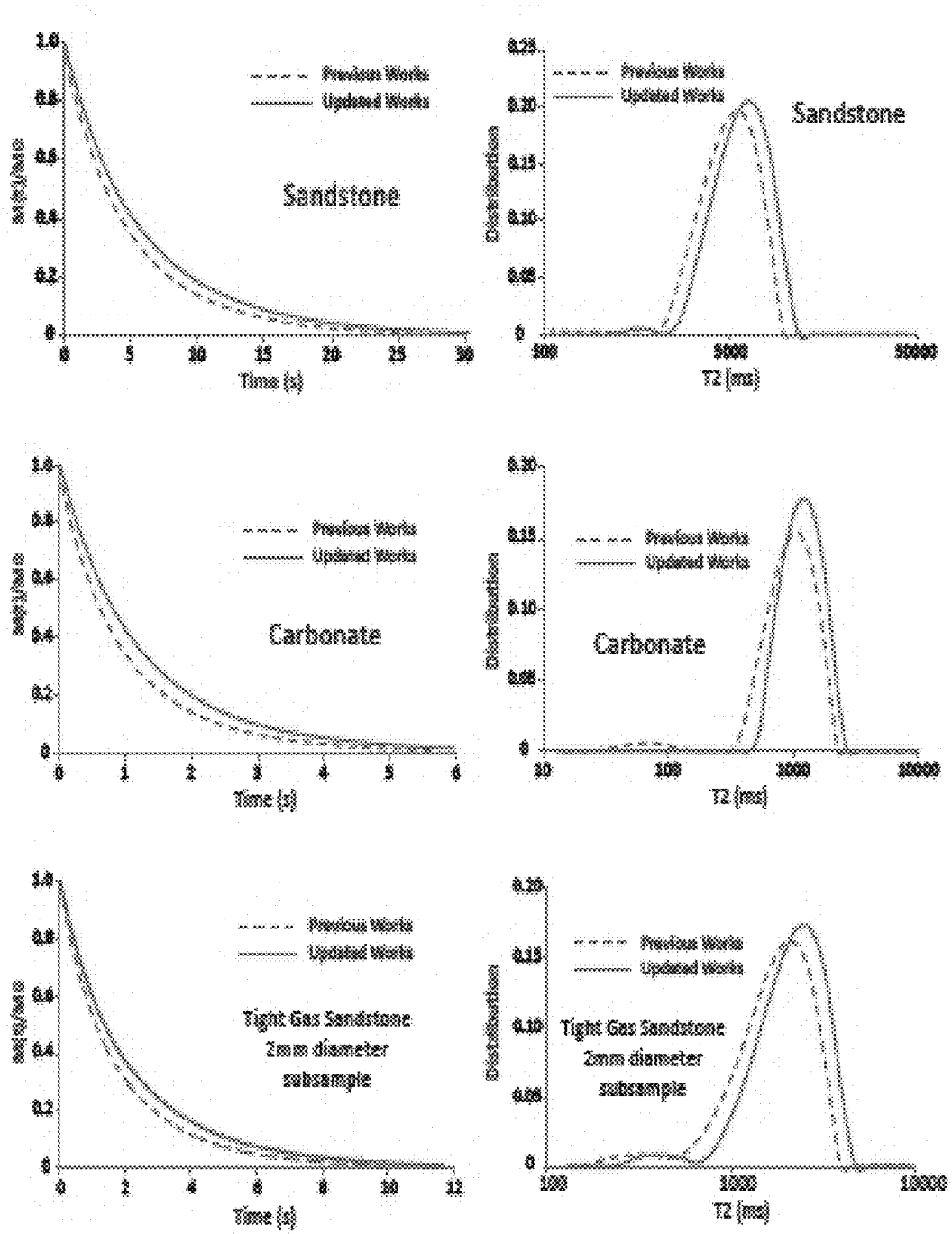
FIG. 6 shows comparisons between previous work and results from embodiments disclosed herein on NMR simulations based on digital images of various rock types (sandstone, carbonate, and tight gas sandstone).

FIG. 6 shows comparisons between previous work and results from embodiments disclosed herein on NMR simulations based on digital images of various rock types (sandstone, carbonate, and tight gas sandstone). The effective corrections of pore space surface areas are apparent from the shifting of the T2 distributions.

Figure 7:
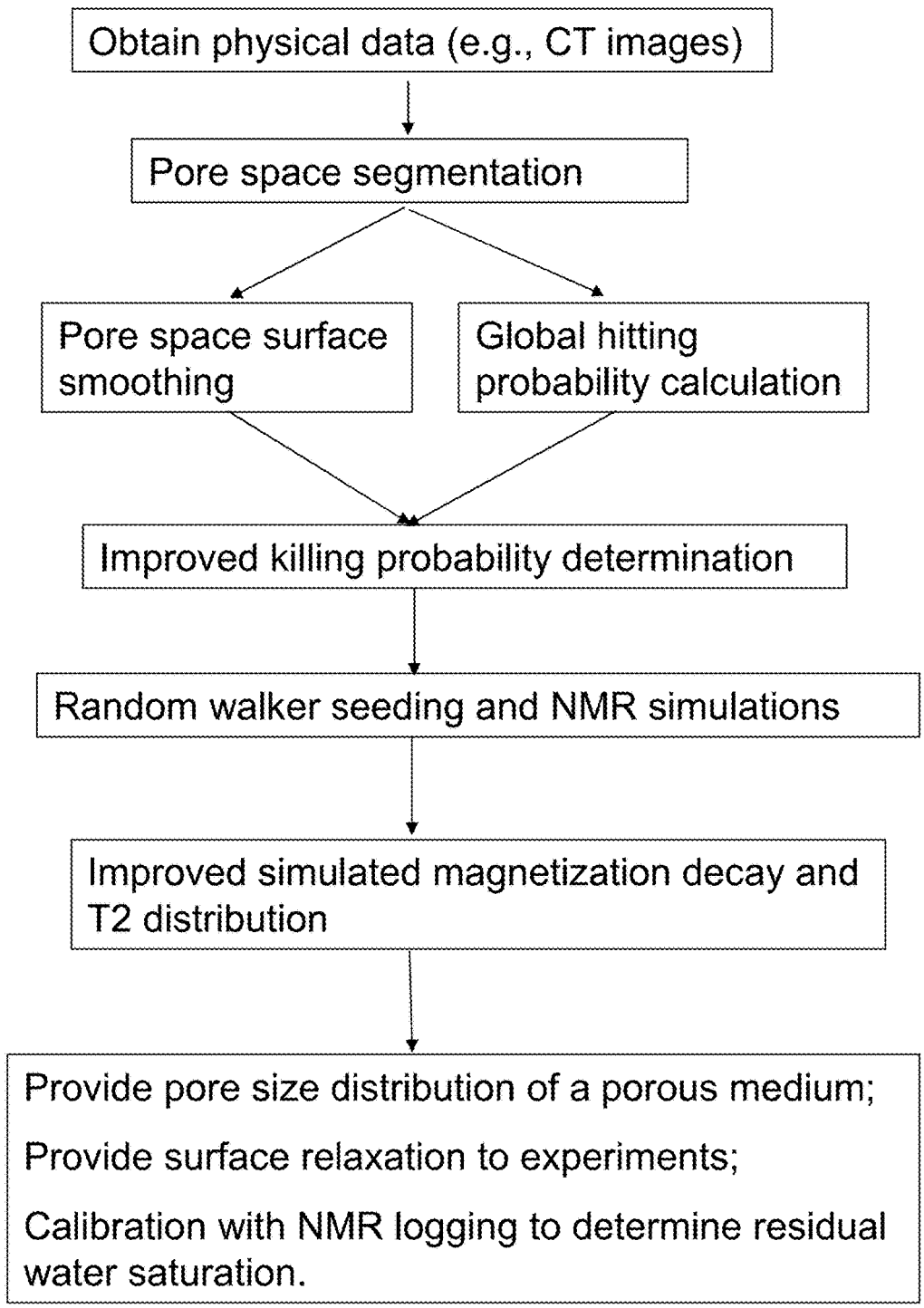
FIG. 7 is a flowchart illustrating a method according to some embodiments disclosed herein.

FIG. 7 is a flowchart of a method according to some embodiments.

Physical data of a porous medium can be obtained, providing 3D geometrical information of the sample. For example, the physical data comprise CT images obtained from CT scanning of the sample. In some other embodiments, other types of physical data containing the 3D geometrical information of the sample can be obtained, such as through other types of imaging technologies.

The physical data such as 3D CT images often are not sufficient to establish an accurate pore size distribution of a porous medium. For example, it may take CT scans of multiple resolutions, such as with nanometer resolutions, to obtain a relatively complete distribution of pore sizes ranging from nanopores to macropores. Even so, CT scans can normally only cover a small sample, otherwise prohibitively large computing power may be needed to obtain a numerical distribution of the pore sizes. The small sample usually cannot be extrapolated to obtain statistics on a larger sample. In addition, CT scanning is usually performed on a static sample without information on the flow dynamics of fluid or hydrocarbon flowing through the pores. As such, imaging alone often cannot be relied upon to obtain accurate estimate of hydrocarbon content in a reservoir during hydrocarbon exploration and extraction.

As such, embodiments disclosed herein provide simulations that can be used to derive properties of the porous media more accurately, with less computing power requirement, and more importantly allow flow properties of the porous media to be derived. The flow properties may include single and multi-phase flow properties of heterogeneous and complex porous media. The single-phase flow properties may include, for example, total porosity, absolute permeability, formation factor. The multi-phase flow properties can include, for example, relative permeability, resistivity index, Amott-Harvey index, USBM wettability index.

In the case of the porous media being a rock, the porous media can have scales ranging from core plugs, whole cores, facies, formations, or reservoirs.

Based on the physical data such as the CT images, the pore spaces can be segmented. A pore space surface smoothing process can be performed, and a global hitting probability calculation can be carried out, as described above.

An improved killing probability determination can then be obtained based on embodiments disclosed herein. The pore spaces can then be seeded with random walkers, and the NMR simulations can be carried out. More accurate simulated magnetization decay and consequently the improved T2 distribution can be obtained through the simulations.

Therefore, more accurate pore size distribution of the porous media can be obtained because the T2 distribution directly reflects the various pore sizes and their volume fraction in the porous media.

Although T2 distributions may also be obtained through NMR experiments. However, due to lack of parameters such as the surface relaxivity, NMR experimental data cannot be employed to easily convert the T2 distribution into the size distribution.

Specifically, the T2 distribution reflects the pore sizes of the porous media but does not provide the actual size in the unit of length. The surface relaxivity may be needed to convert the time unit of T2 into the length unit of pore sizes. However, the surface relaxivity is not usually a measurable parameter. For different type of rocks, the surface relaxivity is usually an empirical value with a specific range.

On the other hand, in the NMR simulations according to some embodiments disclosed herein, the surface relaxivity can be an input parameter that is adjustable. By matching the T2 distribution from NMR simulations with the T2 distribution obtained from NMR experiments, an accurate surface relaxivity can be derived. As such, the NMR simulations disclosed herein can also be used to "calibrate" NMR experiments, to thereby facilitate the conversion of the T2 distribution obtained from NMR experiments into a real size distribution. Therefore, the NMR simulations according to some embodiments disclosed herein are also useful even when NMR experiments are available.

By performing NMR simulations on a same porous media but with various oil/water saturation, the results can be used to calibrate NMR logging and predict residual water saturation in pore spaces. As such, more physical properties of the porous media can be derived based on the NMR simulations disclosed herein.

The smoothed surface area calculations according to some embodiments disclosed herein can provide more accurate pore surface area of the porous media. This can be useful in many areas of applications such as isotherm adsorption, biological tissue characterization, battery material characterization, etc.

The methods can be realized using a software or program code stored on any type of computer-readable medium or memory, such as a storage device including a disk or hard drive. The computer-readable medium may include a non-transitory computer-readable medium or memory, such as computer-readable media that store data for short periods of time like register memory, processor cache and Random Access Memory (RAM). The computer-readable medium may also include non-transitory media or memory, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example.

In addition, the simulation processes and methods disclosed herein can be performed on circuitry that is wired to perform the specific logical functions in the process, and the methods can be realized using a computer system, or implemented in a larger hydrocarbon exploration system. Such a system may include a drilling subsystem as known to those of ordinary skill in the art, a measurement/logging/data collection subsystem, a telemetry subsystem, and a data processing subsystem. Various hardware components in these systems may be known to those of ordinary skill in the art.

Alternatively, the computer system can include computer-readable medium having instructions stored thereon to perform the steps in the methods described above. Those of ordinary skill in the art will recognize that the functional blocks, methods, devices, and systems described in the present disclosure may be integrated or divided into different combinations of systems, devices, and functional blocks. Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time.

A "processor" includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. Various embodiments disclosed herein can be realized via hardware and/or software, such a computer program stored on a memory. For example, a tangible, non-transitory, computer-readable storage medium having instructions stored thereon that, when executed by one or more processors, cause the one or more processors to perform operations including the steps described above.

The memory or storage medium may be any suitable data storage, memory and/or non-transitory computer-readable storage medium, including electronic storage devices such as RAM, ROM, magnetic storage device (hard disk drive or the like), flash, optical storage device (CD, DVD or the like), magnetic or optical disk, or other tangible media such as non-transitory computer-readable medium suitable for storing instructions for execution by the processor. The software instructions can also be contained in, and provided as, an electronic signal, for example in the form of software as a service (SaaS) delivered from a server (e.g., a distributed system and/or a cloud computing system).

All references in the present disclosure are incorporated by reference in their entirety. Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A method of characterizing a porous medium, the method comprising:
   obtaining physical data containing 3D geometrical information for the porous medium;
   determining characteristics of the porous medium using nuclear magnetic resonance (NMR) simulations based on the physical data;
   segmenting pore spaces based on the physical data;
   seeding a plurality of random walkers representing magnetized nuclei into the pore spaces to simulate diffusive Brownian motions of the plurality of random walkers; and
   evaluating a pore space surface area S based on an optimized marching cubes algorithm, wherein said evaluating the pore space surface area S comprises interpolating a virtual smoothed surface along discretized solid-pore interfaces of the porous medium and the plurality of random walkers hitting the grain surface of the porous medium are determined by judging whether the plurality of random walkers cross the virtual smoothed surface; and
   exploring hydrocarbon with higher accuracies based on the characterizing the porous medium including the pore space surface area more accurately evaluated based on the optimized marching cues algorithm.

2. The method of claim 1, wherein the physical data comprise computed tomography (CT) images.

3. The method of claim 2, further comprising segmenting pore spaces based on the CT images.

4. The method of claim 1, wherein a decrease in a number of the plurality of random walkers is used to simulate a transverse decay of magnetization as what would have been measured by an NMR experiment.

5. The method of claim 4, further comprising deriving an interfacial absorption probability at a solid grain surface of the porous medium by deriving a killing probability based on:

$$\gamma = \frac{\rho \epsilon^2 S}{6 D_0 h V} \quad \text{(i)}$$

wherein:
   $\gamma$ is the killing probability for the plurality of random walkers to be absorbed by the grain surface of the porous medium;
   $D_0$ is bulk fluid diffusivity and $\in$ is a diffusion distance of the plurality of random walkers within a time step, as described in law of Brownian motion of spatial diffusive particles in a 3D space;
   h is a global probability for the plurality of random walkers to hit the grain surface of the porous medium;
   $\rho$ is surface relaxivity of, S is pore space surface area of, and V is pore space volume of the porous medium.

6. The method of claim 5, wherein the global probability h is calculated based on $$h = \Sigma_{i=1}^{N}(1-Z_i)(h_s \Sigma_{s=1}^{6} Z_i^s + h_c \Sigma_{c=1}^{8} Z_i^c + h_e \Sigma_{e=1}^{12} Z_i^e) \quad \text{(ii)}$$

where $Z_i$ is voxel registration of the ith voxel of a 3D image with $Z_i=0$ for a void and $Z_i=1$ for a solid grain; $Z_i^s$ ($Z_i^c$ or $Z_i^e$) are the 6 (8 or 12) sided (corner or edge) neighboring voxels of $Z_i$, and $h_s$, $h_c$ and $h_e$ are constant probabilities of the plurality of random walkers in voxel $Z_i$ jumping into sided, corner and edge voxels, respectively.

7. The method of claim 4, further comprising obtaining a pore size distribution based on the simulated transverse decay of magnetization.

8. The method of claim 4, further comprising determining a surface relaxation parameter of the porous medium based on the NMR simulations.

9. The method of claim 8, further comprising calibrating the NMR experiment based on the derived surface relaxation parameter.

10. The method of claim 4, further comprising deriving one or more physical parameters of the porous medium based on the NMR simulations.

11. The method of claim 10, wherein the physical parameters comprise multi-phase flow properties of the porous medium.

12. The method of claim 11, further comprising applying the physical parameters in hydrocarbon content estimation, exploration, extraction, or logging.

13. The method of claim 1, wherein the porous medium comprises a rock.

14. The method of claim 13, wherein the rock is an unconventional reservoir rock having a high surface-to-volume ratio (SN).

15. The method of claim 14, wherein the reservoir rock comprises at least one of a carbonate stone, or a shale.

16. A non-transitory computer-readable medium having instructions stored thereon, the instructions comprising:
   obtaining physical data containing 3D geometrical information for the porous medium;
   determining characteristics of the porous medium using nuclear magnetic resonance (NMR) simulations based on the physical data;
   segmenting pore spaces based on the physical data;
   seeding a plurality of random walkers representing magnetized nuclei into the pore spaces to simulate diffusive Brownian motions of the plurality of random walkers; wherein a decrease in a number of the plurality of random walkers is used to simulate a transverse decay of magnetization as what would have been measured by an NMR experiment;
   deriving an interfacial absorption probability at a solid grain surface of the porous medium by deriving a killing probability based on:

$$\gamma = \frac{\rho \epsilon^2 S}{6 D_0 h V} \quad \text{(i)}$$

wherein:
   $\gamma$ is the killing probability for the plurality of random walkers to be absorbed by the grain surface of the porous medium;
   $D_0$ is bulk fluid diffusivity and $\in$ is a diffusion distance of the plurality of random walkers within a time step, as described in law of Brownian motion of spatial diffusive particles in a 3D space;
   h is a global probability for the plurality of random walkers to hit the grain surface of the porous medium;
   $\rho$ is surface relaxivity of, S is pore space surface area of, and V is pore space volume of the porous medium; and
   exploring hydrocarbon with higher accuracies based on the more accurately-derived interfacial absorption probability at the solid grain surface of the porous medium.

17. The non-transitory computer-readable medium of claim 16, wherein the physical data comprise computed tomography (CT) images, and wherein the instructions further comprise:
    segmenting pore spaces based on the CT images.

18. A hydrocarbon exploration system configured to perform a method comprising:
    obtaining physical data containing 3D geometrical information for the porous medium;
    determining characteristics of the porous medium using nuclear magnetic resonance (NMR) simulations based on the physical data;
    segmenting pore spaces based on the physical data;
    seeding a plurality of random walkers representing magnetized nuclei into the pore spaces to simulate diffusive Brownian motions of the plurality of random walkers;
    evaluating a pore space surface area S based on an optimized marching cubes algorithm, wherein said evaluating the pore space surface area S comprises interpolating a virtual smoothed surface along discretized solid-pore interfaces of the porous medium and the plurality of random walkers hitting the grain surface of the porous medium are determined by judging whether the plurality of random walkers cross the virtual smoothed surface; and
    exploring hydrocarbon with higher accuracies based on the characteristics of the porous medium including the pore space surface area more accurately evaluated based on the optimized marching cues algorithm.

19. The hydrocarbon exploration system of claim 18, wherein a decrease in a number of the plurality of random walkers is used to simulate a transverse decay of magnetization as what would have been measured by an NMR experiment, and wherein the method further comprises:
    deriving one or more physical parameters of the porous medium based on the NMR simulations, wherein the physical parameters comprise multi-phase flow properties of the porous medium; and
    applying the physical parameters in hydrocarbon content estimation, exploration, extraction, or logging.

* * * * *